(12) United States Patent
Shimanuki (10) Patent No.: US 7,238,850 B2
(45) Date of Patent: Jul. 3, 2007

(54) HEMOSTASIS TOOL HAVING BLOOD DIFFUSION AND ABSORPTION ABILITIES

(75) Inventor: Takeshi Shimanuki, Saitama-Ken (JP)

(73) Assignee: Kabushiki Kaisha Meditech, Saitama-Shi, Saitama-Ken (JP)

( * ) Notice: Subject to any disclaimer, the term of this patent is extended or adjusted under 35 U.S.C. 154(b) by 0 days.

(21) Appl. No.: 11/360,461

(22) Filed: Feb. 23, 2006

(65) Prior Publication Data

US 2007/0100271 A1   May 3, 2007

(30) Foreign Application Priority Data

Nov. 2, 2005   (JP)   ............... 2005-319448

(51) Int. Cl.
*A61F 13/00*  (2006.01)
*A61F 15/00*  (2006.01)

(52) U.S. Cl. .................. 602/56; 602/43; 602/44

(58) Field of Classification Search ............ 602/41–44, 602/48, 50, 56; 128/888, 889; 424/443–447; 604/304, 307, 543, 358, 368, 374, 377, 378, 604/385.101

See application file for complete search history.

(56) References Cited

U.S. PATENT DOCUMENTS 4,411,660 A * 10/1983 Dawn et al. ............... 604/396
5,204,110 A *  4/1993 Cartmell et al. ........... 424/443
6,258,996 B1 *  7/2001 Goldman ................... 604/368
2003/0040691 A1 *  2/2003 Griesbach et al. ........... 602/45
2005/0049566 A1 *  3/2005 Vukos et al. ............... 604/378
2006/0142719 A1 *  6/2006 Vogt et al. ................. 604/378

FOREIGN PATENT DOCUMENTS

JP         H03-23173       3/1991

* cited by examiner

Primary Examiner—Justine R. Yu
Assistant Examiner—K C Matter
(74) Attorney, Agent, or Firm—Flynn, Thiel, Boutell & Tanis, P.C.

(57) ABSTRACT

A hemostasis tool is provided for stopping bleeding by absorbing blood from the wound and having blood diffusion and absorption abilities, which includes a lamination comprising a water-permeable inner material on a wound side, a water-impermeable outer material on a side departing from the wound side, a pulp-cotton laminated body between the inner and outer materials, a crust between the pulp-cotton laminated body and the water-impermeable outer material for diffusing the blood that has passed through the water-permeable inner material and the pulp-cotton laminated body, and a polymer for absorbing the blood diffused by the crust. Instead of the pulp-cotton laminated body, a synthesis fiber laminated body can be utilized in the hemostasis tool having a laminated structure. The hemostasis tool serves to actively diffuse transmitted blood by a crust disposed in the intermediate layer of a hemostasis tool, and to improve the absorbing ability of the blood with a polymer that is polymeric absorbing material disposed at an outer part than the crust.

14 Claims, 5 Drawing Sheets

HEMOSTASIS TOOL HAVING BLOOD DIFFUSION AND ABSORPTION ABILITIES

FIELD OF THE INVENTION

This invention relates to hemostatic tools having blood diffusion and absorption abilities, and more particularly to a hemostatic tool having blood diffusion and absorption abilities wherein a crust positioned in an intermediate layer effectively diffuses the blood passing therethrough and a polymer is provided which is a polymeric absorbing material positioned on an outer side of the crust that considerably improves the blood absorption ability.

BACKGROUND ART

In the state of the art, various hemostatic tools are utilized depending on the amount of blood from wound. For example, in case the amount of blood from a wound is small, bandage, gauze, and adhesive plaster are utilized. In case the amount of blood is large, tourniquet and triangular bandages are generally utilized for emergency treatment, since the bandage, gauze, and adhesive plaster are not enough to deal with the large amount of blood.

Also, as a transportation means advances, there is an increase in traffic accidents, in particular automobile or train accident. Recently, there was a large-scale earthquake disaster in Kansai region. Under the circumstances, some people unfortunately encounter these accidents or disaster and bleed in large amount.

SUMMARY OF THE INVENTION

As to the problems to be solved by the invention, in using conventional hemostatic tools, it requires considerable medical knowledge and training to use the tourniquet or triangular bandage that is utilized for temporary emergency treatment in cases where the bleeding from a wound is large in amount.

Another hemostatic tool to cure or treat the wound after bleeding occurs is disclosed in JP No. H03-23173.

JP No. H03-23173 discloses a first pulp-cotton integrated body that absorbs blood, a second pulp-cotton laminated body that includes a layer for dispersion and absorption of serum in the blood, a powdered coagulant, and a scab over the surface of the wound to stop bleeding.

According to JP No. H03-23173 when the first pulp-cotton laminated body absorbs the blood, this causes a blood clot to be formed at the center and a supersaturation portion of the blood to be formed around the clot. The pulp-cotton laminated body with layers absorbs exclusively the serum in the blood. Absorption of the serum by the pulp-cotton laminated body with layers is however concentrated adjacent the clot that is formed.

That is, the pulp-cotton laminated body with layers absorbs the serum without sufficient diffusion of the serum.

As a result, in cases where the amount of bleeding is large, the diffusion and absorption abilities of the pulp-cotton laminated body with layers are not fully utilized, wherein the serum undesirably stays or resides adjacent the clot. In case external pressure is applied to the pulp-cotton laminated body, the serum that stays moves toward the clot, i.e. counterflows. Improvement is desired to obviate the problems with this prior art.

Further, although JP No. H03-23173 discloses the constitution in which the pulp-cotton laminated body with layers absorbs the serum, it is merely utilizing the diffusion and absorption abilities of the pulp-cotton laminated body with layers that it inherently has. None of the methods is disclosed as positively diffusing the serum.

The subject of the present invention is to effectively diffuse the blood with the crust in the intermediate layer of the hemostatic tool and to improve the blood absorption ability thereof with the polymer as a polymeric absorbing material.

As to means to solve the problems with the prior art, in order to obviate the above-mentioned inconveniences, the present invention provides a hemostatic tool for stopping bleeding by absorbing blood from the wound, which includes a lamination comprising a water-permeable inner material on a wound side, a water-impermeable outer material on a side departing from the wound side, a pulp-cotton laminated body between the inner and outer materials, a crust between the pulp-cotton laminated body and the water-impermeable outer material for diffusing the blood that has passed through the water-permeable inner material and the pulp-cotton laminated body, and a polymer for absorbing the blood diffused by the crust.

The present invention also provides a hemostatic tool for stopping bleeding by absorbing blood from the wound, which includes a lamination comprising a water-permeable inner material on a wound side, a water-impermeable outer material on a side departing from the wound side, a synthetic fiber laminated body between the inner and outer materials, a crust between the synthetic fiber laminated body and the water-impermeable outer material for diffusing the blood that has passed through the water-permeable inner material and the synthetic fiber laminated body, and a polymer for absorbing the blood diffused by the crust.

As thus described, the present invention provides a hemostatic tool for stopping bleeding by absorbing blood from the wound, which includes a lamination comprising the water-permeable inner material on the wound side, the water-impermeable outer material on the side departing from the wound side, the pulp-cotton laminated body between the inner and outer materials, the crust between the pulp-cotton laminated body and the water-impermeable outer material for diffusing the blood that has passed through the water-permeable inner material and the pulp-cotton laminated body, and the polymer for absorbing the blood diffused by the crust. Accordingly, the crust in the intermediate portion of the layer of the hemostatic tool effectively diffuses the blood passing therethrough, taking advantage of the whole region of the hemostatic tool to effect the full absorption ability. Also, the polymer serves as polymeric absorbing material positioned outside of the crust that considerably improves the absorption ability of the blood. In addition, the polymer absorbs the blood, swells, and gelates. Accordingly, the blood absorbed by the polymer does not move out toward the water-permeable inner material on the wound side, i.e. no-counterflowing, in case external pressure is applied to the water-impermeable outer material. This does not affect the formation of the scab that quickly covers the wound for rapid hemostasis, which is advantageous in practical use.

In addition, the present invention also provides a hemostatic tool for stopping bleeding by absorbing blood from the wound, which includes a lamination comprising the water-permeable inner material on the wound side, the water-impermeable outer material on the side departing from the wound side, the synthetic fiber laminated body between the inner and outer materials, the crust between the synthetic fiber laminated body and the water-impermeable outer material for diffusing the blood that has passed through the water-permeable inner material and the synthetic fiber laminated body, and the polymer for absorbing the blood diffused by the crust. Accordingly, the polymer serves as polymeric absorbing material that considerably improves the blood absorption ability. The use of the synthetic fiber laminated body applied to the hemostatic tool blocks the flow of the clot and the erythrocyte for rapid covering of the wound by the scab, and allows the flow of the other components such as serum so as to quickly cover the wound by the scab for immediate hemostasis. Further, owing to the smooth surface of the synthetic fiber, the use of the synthetic fiber laminated body, instead of the pulp-cotton lamination, can avoid the serum from staying adjacent the clot. In case external pressure is applied to the hemostatic tool when the serum stays adjacent the clot, the synthetic fiber lamination has a higher elasticity than the pulp-cotton lamination and permits the serum that stays to flow to the polymer side, which avoids undesirable counterflowing of the staying serum to the clot side.

According to the best mode of the present invention, when the hemostatic tool is applied to the wound, the blood from the wound passes through the water-permeable inner material and the pulp-cotton laminated body to the inner side of the crust. The blood reaching the crust is diffused substantially in the direction orthogonal to the passing direction in the crust, i.e. in the dispersion direction. Then the blood diffused by the crust reaches the polymer and is absorbed by the polymer that swells and gelates.

In addition, according to the present invention, when the hemostatic tool is applied to the wound, the blood from the wound passes through the water-permeable inner material and the synthetic fiber laminated body to the inner side of the crust. The blood reaching the crust is diffused substantially in a direction orthogonal to the passing direction in the crust, i.e. in the dispersion direction. Then the blood diffused by the crust reaches the polymer and is absorbed by the polymer that swells and gelates.

BRIEF DESCRIPTION OF THE DRAWINGS

Embodiments of the present invention are described in detail below with reference to the following drawings.

FIGS. 10A–10D are schematic plan views of the polymer formed of the sheet-shaped member according to the eighth embodiment of the present invention, wherein

Certain terminology will be used in the following description for convenience and reference only, and will not be limiting. For example, the words "upwardly", "downwardly", rightwardly", "leftwardly" will refer to directions in the drawings to which reference is made. The words "inwardly" and outwardly" will refer to directions toward and away from, respectively, the geometric center of the arrangement and designated parts thereof. Said terminology will include the words specifically mentioned, derivatives thereof, and words of similar import.

DETAILED DESCRIPTION

Figure 1:
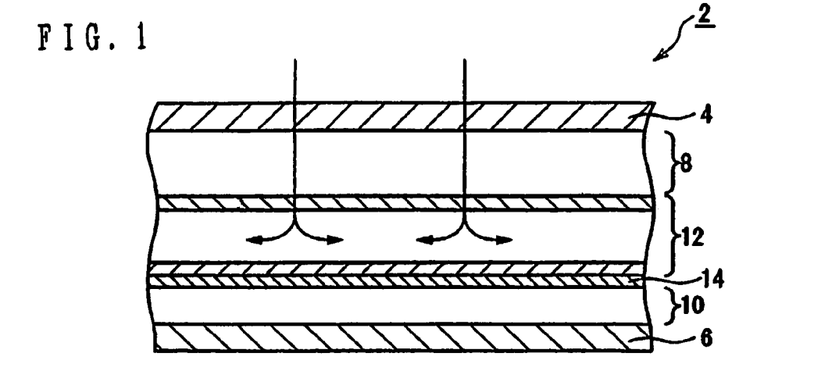
FIG. 1 is a schematic cross-sectional view of the hemostatic tool with blood diffusion and absorption abilities according to the first embodiment of the present invention.
Figure 2:
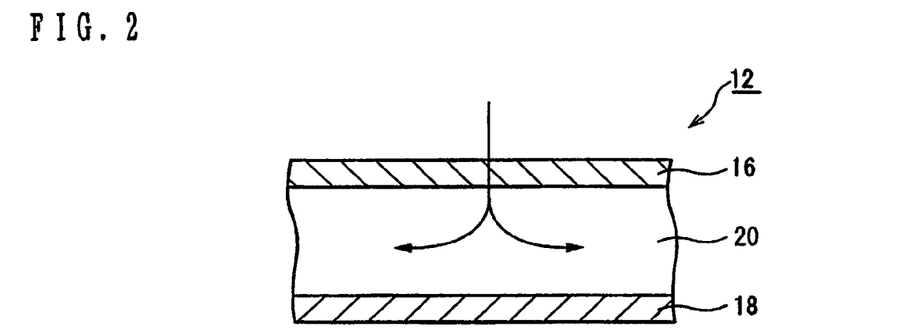
FIG. 2 is a schematic enlarged cross-sectional view of the crust.

FIG. 1 and FIG. 2 illustrate a first embodiment of the present invention, wherein FIG. 1 shows a hemostatic tool 2 having blood diffusion and absorption abilities.

The hemostatic tool 2 is used to stop bleeding by absorbing the blood from the wound.

The hemostasis tool 2 includes a water-permeable inner material 4 on an inner side or a wound side, and a water-impermeable outer material 6 on a side farthest from the wound side.

Between the water-permeable inner material 4 and the water-impermeable outer material 6, a first pulp-cotton laminated body 8 is disposed on the water-permeable inner material 4, as shown in FIG. 1. A second pulp-cotton laminated body 10 is disposed on the water-impermeable outer material side. Between the first and second laminated bodies 8 and 10, a crust 12 and a polymer 14 are positioned. The crust 12 diffuses the blood that has passed through the water-permeable inner material 4 and the first pulp-cotton laminated body 8. The polymer 14 absorbs the blood diffused by the crust 12.

In the above constitution of the hemostatic tool 2, the second pulp-cotton laminated body 10 and the polymer 14 in particular are separated and merely laminated. The second pulp-cotton laminated body 10 and the polymer 14 may however be a single-piece construction.

The second pulp-cotton laminated body 10 on the side of the water-impermeable outer material 6 is provided to improve both protection from the external pressure to the polymer 14 after swelling and gelation and maintenance of the polymer 14. If the other materials such as crust 12 and the water-impermeable outer material 6 are provided with such abilities, the second pulp-cotton lamination 10 may be eliminated.

More particularly, the water-permeable inner material 4 can be any water-permeable material, such as water-permeable film and nonwoven fabric. In this first embodiment, the water-permeable inner material 4 comprises a water-permeable film.

Also, the water-impermeable outer material 6 can be a water-permeable material, such as water-impermeable film and water-resistant paper. In this first embodiment of the present invention, the water-impermeable outer material 6 comprises a water-impermeable film formed by a sheet member such as a vinyl sheet.

The first and second pulp-cotton laminated bodies 8 and 10 are mainly made of pulp-cotton. The pulp-cotton is an agglomeration of short fibers, which short fibers do not substantially tangle with each other and have the property of being brittle and easy to collapse. On this account, the pulp-cotton without tangle is laminated and compacted to a preferable thickness so as to form the first and second laminated bodies 8 and 10.

Referring to FIG. 2, the crust 12 includes two sheets of layers made of paper, i.e. first and second cortical layers 16 and 18, and a pulp-cotton laminated body 20 interposed therebetween. The first cortical layer 16 is disposed on the side of the water-permeable inner material 4 and the second cortical layer 18 on the side of the water-impermeable outer material 6.

The above-mentioned first and second cortical layers 16 and 18 are any material with permeability and maintenance ability as the pulp-cotton laminated body 20, and are not limited to the paper-made. They can be replaced by the water-permeable film or the nonwoven fabric.

The pulp-cotton laminated body 20 is chemically bound by the fabrics being added with some water, pressurized and dried.

Further, the polymer 14 includes a high polymeric absorbent in which granular or powdery ones are formed into a sheet shape. The polymer 14 has a strong hydrophilicity; has the absorption ability which absorbs the liquid in weight by 60 times with respect to its own weight; maintains the absorbed liquid; and swells and gelates.

As shown in FIG. 1, laminated are the following, in turn from the wound side: the water-permeable inner material 4; the first pulp-cotton laminated body 8; the crust 12; the polymer 14; the second pulp-cotton laminated body 10; and the water-impermeable outer material 6. Outer portions of the water-permeable inner material 4 and the water-impermeable outer material 6 are adhered with a method such as a sheet-heel method so as to form the hemostatic tool.

Incidentally, the composition of the blood involves 55% of plasma and 45% of blood cell. The substances that coagulate the blood are fibrinogen in the plasma and the blood cell. Other components other than fibrinogen in plasma, i.e. serum (liquid), are worthless for blood coagulation. Serum is not involved in blood coagulation, rather affecting and blocking the blood coagulation. On this account it is required to leave fibrinogen in plasma and remove serum quickly for blood coagulation.

Thus in the specification of the present invention, "absorption of the blood" can be replaced by "absorption of serum (liquid) in plasma of the blood".

The blood can be divided into coagulable clot and uncoagulable serum. In particular, the clot is a dark red coagulation formed by the solidification of the blood, in which erythrocyte, leucocyte, and blood platelet tangle in small net structures of fibrin. Serum is a supernatant obtained by removing cell element and coagulation element when the blood is left standing in a container, which is a pale yellow transparent liquid that includes immune antibody, various nutrients, and waste products.

It is the purpose of the hemostatic tool 2 of the present invention to isolate the blood coagulation elements from the uncoagulation elements, leaving the clot on the wound, and quickly absorbing and diffusing the serum (in other words, the uncoagulation liquid) by the crust 12, so as to accomplish the situation where a clot is quickly formed over the wound.

Operation of the embodiment of the present invention is described below.

In using the hemostatic tool 2, this tool 2 is adhered onto the wound so that wound part is positioned generally at the center of the water-permeable inner material 4 of the hemostatic tool 2.

Then, as indicated by arrows in FIG. 1, the bleeding from the wound passes through the water-permeable inner material 4 and the first pulp-cotton laminated body 8 to the first cortical layer 16 inside of the crust 12. The blood reaching the first cortical layer 16 is diffused substantially in a direction orthogonal to the passing direction in the pulp-cotton laminated body 20, i.e. in the disperse direction.

The blood diffused by the pulp-cotton laminated body 20 reaches the polymer 14 after passing the second cortical layer 18, and is absorbed by the polymer 14 that swells and gelates.

Accordingly, the crust 12 positioned in the intermediate layer portion of the hemostatic tool 2 effectively diffuses the blood, taking advantage of the wide area of the hemostatic tool 2 to effect the full absorption ability.

In addition, owing to the positioning of the polymer 14 as a polymeric absorbing material outward of the crust 12, the blood absorption ability is considerably improved.

Further, the polymer 14 absorbs the blood, swells, and gelates. Accordingly, the blood absorbed by the polymer 14 does not move out toward the water-permeable inner material 4 on the wound side, i.e. no-counterflowing, in case external pressure is applied to the water-impermeable outer material 6. This does not affect the formation of the scab that quickly covers the wound for rapid hemostasis, which is advantageous in practical use.

Next, a second embodiment of the present invention is described below.

The second embodiment of the present invention is characterized by use of an artificial skin or suture material for the water-permeable inner material on the wound side.

More particularly, after applying the hemostatic tool onto the wound, the water-permeable inner material utilizing the artificial skin or the suture material is used to contribute to the formation of the scab. After the scab is formed, the hemostatic tool can be removed while only the water-permeable inner material is left on the wound.

Generally, there is a possibility that the scab may not be formed when the wound is large. Even when the scab is formed, it requires much time.

To obviate this inconvenience, the water-permeable inner material of the hemostatic tool is allowed to contribute, at least partially, to the formation of the scab. This permits rapid formation of the scab to achieve quicker hemostasis.

Figure 3:
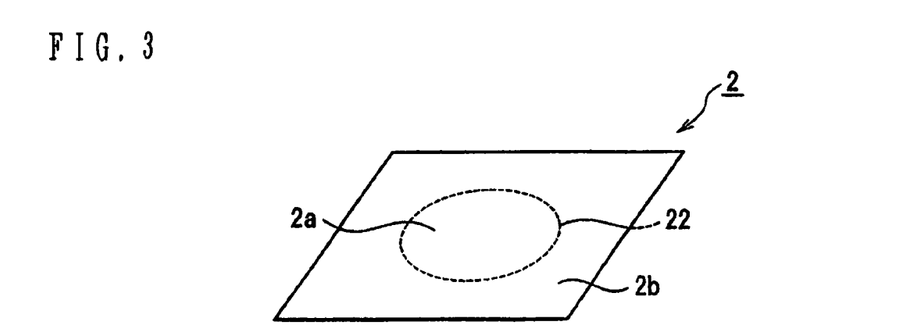
FIG. 3 is a schematic perspective view of the hemostatic tool according to the third embodiment of the present invention.

FIG. 3 illustrates a third embodiment of the present invention. The same reference characters are hereinafter utilized for features identical in function to those described in the first embodiment.

The third embodiment is characterized by a perforated tear-off line on the hemostatic tool 2.

More particularly, when lamination from the water-permeable inner material to the water-impermeable outer material is formed for the hemostatic tool 2, the tear-off line 22 is defined, e.g. in a circle shape, so as to tear off the hemostatic tool 2 in a certain shape, as shown in FIG. 3.

At this time, when forming the hemostatic tool 2 in the circular shape defined by the tear-off line 22, the tear-off line 22 is formed by an additional adhesive method such as the sheet-heel method so as to avoid unbinding of the lamination in which the hemostatic tool 2 is detached from the tear-off line 22.

When applying the hemostatic tool 2 onto the wound, as shown in FIG. 3, the hemostatic tool 2 is placed so that the center of the circular tear-off line 22 is positioned over the wound. In two portions 2a and 2b which are defined by the tear-off line 22, the part 2b of the hemostatic tool 2, on an outer circumference side or a portion departing from the wound, is torn off from the part 2a, the circular remaining portion on an inner circumference side. Only the part 2a defined by the tear-off line 22 remains on the wound, which can be utilized efficiently while eliminating waste of the hemostatic tool 2, and is advantageous in economical viewpoint.

Alternatively, if square tear-off lines are formed on the hemostatic tool in multiple numbers, the number of squares may be increased or decreased in accordance with the size of the wound to which the tool is applied, which tool can be utilized more economically while eliminating waste of the hemostatic tool 2.

Further, the tear-off line 22 is configured with the additional adherent method such as the sheet-heel method, such that unbinding of the lamination is avoided when the hemostatic tool 2 is detached from the tear-off line 22, and leaking of the blood from the tear-off line 22 is also avoided, which is advantageous in practical use.

Figure 4:
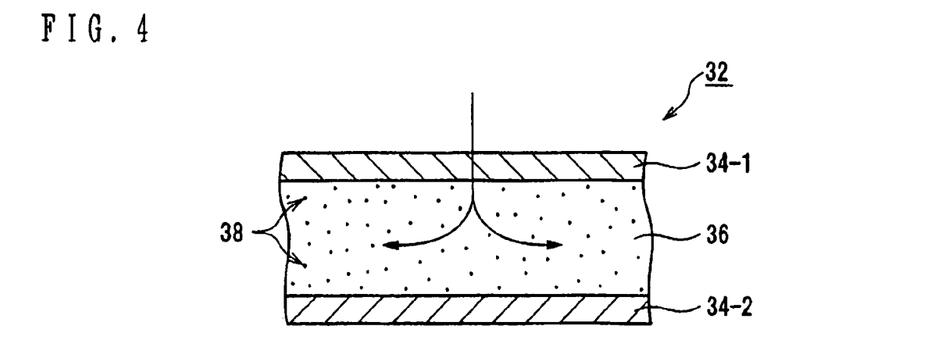
FIG. 4 is a schematic perspective view of the hemostatic tool according to the fourth embodiment of the present invention.
Figure 5:
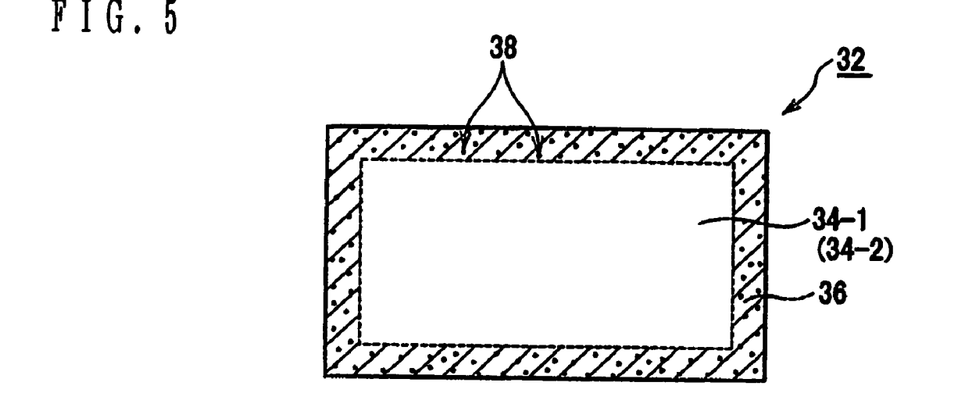
FIG. 5 is a schematic plan view of the crust.

FIGS. 4 and 5 illustrate a fourth embodiment of the present invention.

The fourth embodiment is characterized by a charcoal powder 38 in at least a part of the pulp-cotton laminated body 36 between first and second cortical layers 34-1, 34-2.

More particularly, when forming the crust 32 with the two sheets of the paper-made first and second cortical layers 34-1, 34-2 and the pulp-cotton laminated body 36 interposed therebetween, the charcoal powders 38 may be uniformly dispersed in at least a part or whole of the pulp-cotton laminated body 36. Here, as shown in FIG. 4, the charcoal powders 38 are dispersed adjacent the outer rim of the pulp-cotton laminated body 36.

Accordingly, the charcoal powder 38 in at least the part of the laminated body 36 of the crust 32 serves to block a bad smell from any blood that has reached adjacent to the outer rim of the laminated body 36 after absorption and diffusion. This achieves a deodorization and antibacterial effect, and a negative air ions effect can be expected, which is easy on the human body.

When dispersing the charcoal powder 38, in addition to the pulp-cotton laminated body 36 between the first and second cortical layers 34-1, 34-2 of the crust 32, the charcoal powder 38 can also be dispersed in the pulp-cotton laminated body outside of the crust.

Figure 6:
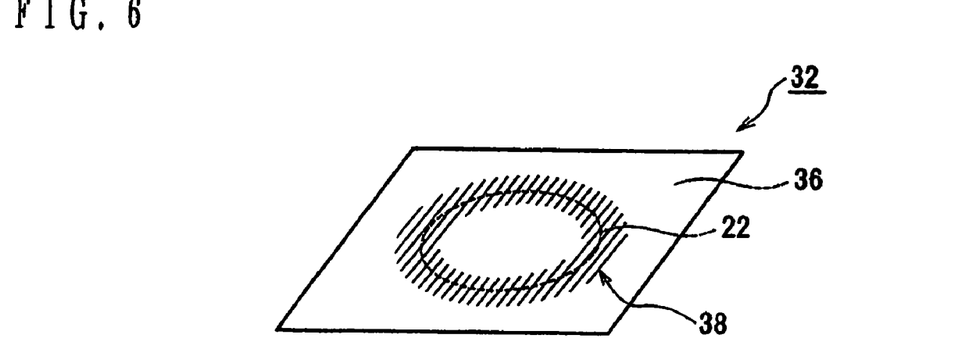
FIG. 6 is a schematic perspective view of the hemostatic tool in combination of the third and fourth embodiments of the present invention.

Further, as shown in FIG. 6, by combining the charcoal powder 38 of the fourth embodiment and the tear-off line 22 of the third embodiment, the charcoal powder 38 can be dispersed in outer and inner portions of the tear-off line 22 as a special configuration.

More particularly, when the charcoal powder 38 in the laminated body 36 of the crust 32 is dispersed in the outer and inner portions of the tear-off line 22, even if the blood reaches the tear-off line 22 after absorption and diffusion, the dispersed charcoal powder 38 blocks the bad smell of the blood with reliability, which achieves the deodorization and antibacterial effect for the blood to contribute to easiness on the human body. In addition, the dispersed charcoal powder 38 prevents leaking of the blood from the tear-off line 22, when the hemostatic tool is removed from the tear-off line 22.

Figure 7:
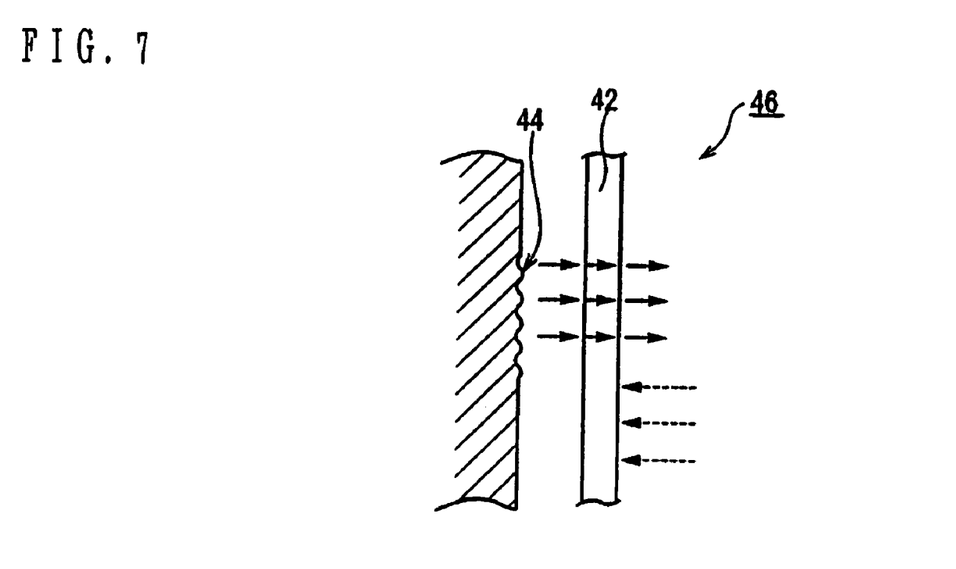
FIG. 7 is a schematic enlarged view when the hemostatic tool 46 is applied to the wound 44 formed in the human body according to the fifth embodiment of the present invention.

FIG. 7 illustrates a fifth embodiment of the present invention.

The fifth embodiment is characterized by a semi-permeable membrane structure in which the water-permeable inner material 42 comprised of the water-permeable film allows passing of the blood from the side of the wound 44 and blocks the liquid from the outside.

More particularly, when the hemostatic tool 46 is applied onto the wound 44 formed in the human body, the inner material 42 of the semi-permeable membrane structure allows the blood from the wound 44 to penetrate the hemostatic tool 46 (indicated by solid lines in FIG. 7) and blocks passing of the liquid from the outside, i.e. blocking of counterflowing blood that is once absorbed in the hemostatic tool 46 (indicated by dashed lines in FIG. 7).

Accordingly, owing to the inner material 42 of the semi-permeable membrane structure, the hemostatic tool 46 effectively absorbs the blood from the wound 44, and the counterflowing blood, which is the liquid from outside once absorbed by the tool 46, is securely blocked. Thereby, the wound is not exposed to the counterflow blood, so that the scab is formed quickly which covers the wound 44 for rapid hemostasis.

Figure 8:
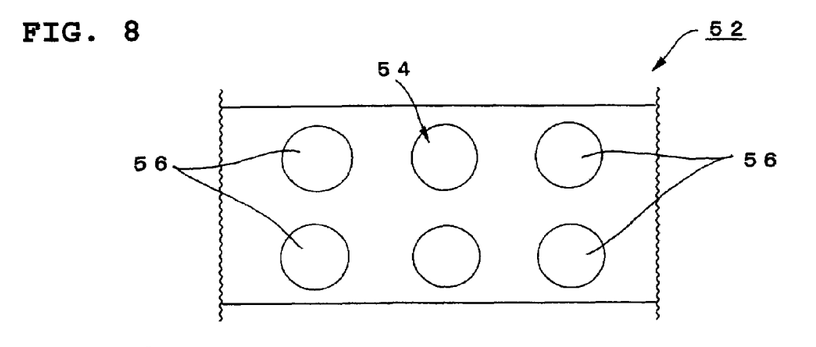
FIG. 8 is a schematic plan view of the polymer formed of the sheet-shaped member according to the sixth embodiment of the present invention.

FIG. 8 illustrates a sixth embodiment of the present invention.

The sixth embodiment is characterized by a penetrating section 54 defined in a polymer 52 or the polymeric absorbing material that is formed of a sheet-shaped member. The penetrating section 54 includes a plurality of through-hole sections 56 that are formed in circular shapes having the same diameters.

More particularly, when forming the penetrating section 54, i.e. a plurality of through-hole sections 56 in the circular shapes and having the same diameters in the polymer 52, the through-hole sections 56 are spaced at regular intervals, as shown in FIG. 8.

When forming the through-hole sections 56 at regular intervals, these can be aligned not only in rows as shown in FIG. 8, but in a staggered formation.

Accordingly, when the hemostatic tool is applied onto the wound so that the wound is positioned at the center of the water-permeable inner material of the hemostatic tool, the bleeding from the wound passes through the water-permeable inner material and the first pulp-cotton laminated body to the first cortical layer inside of the crust. The blood reaching the first cortical layer is diffused substantially in a direction orthogonal to the passing direction in the pulp-cotton laminated body, i.e. in the dispersion direction.

The blood diffused by the pulp-cotton laminated body reaches the polymer 52 after passing the second cortical layer, and is absorbed by the polymer 52 that swells and gelates.

Due to the formation of the circular through-hole sections 56 of the same diameters in the polymer 52 at regular intervals, the through-hole sections 56 function as storage space to store therein the surplus blood, if any, that is not absorbed by the polymer 52, which surplus blood gelates so as to be in a low viscosity.

Thereby, the through-hole sections 56 formed in the polymer 52 function as the expansion swelling space for the polymer 52 absorbing the blood and as the storage space to store the surplus blood gelated in the low viscosity after absorption. Correspondingly to these parts not including the polymer 52, the absorption ability of the polymer 52 is considerably improved.

Due to formation of the through-hole sections 56 in the polymer 52 for improving the blood absorption ability, the blood absorbed by the polymer 52 or the surplus blood stored in the gelate state that has a low viscosity does not move out toward the water-permeable inner material on the wound side, i.e. no-counterflowing, in the case where external pressure is applied to the water-impermeable outer material. This does not affect the formation of the scab that quickly covers the wound for rapid hemostasis, which is advantageous in practical use.

Further, formation of the through-hole sections 56 in the polymer 52 still contributes to improvement of the blood absorption ability, which also contributes to saving the cost of the material corresponding to the through-hole sections 56, and is advantageous in an economical viewpoint.

Still further, instead of the penetrating section including through-hole sections in the polymer, liquid absorption paper with temporary absorption ability can be positioned at a portion of the second cortical layer of the pulp-cotton laminated body on the water-permeable inner material side, and this liquid absorption paper is provided with the penetrating section including the plural circular through-hole sections having the same diameters as a variation of the embodiment.

Accordingly, the liquid absorption paper temporarily absorbs the blood from the water-permeable inner material side and the quick diffusion is achieved utilizing the penetrating section, so that the blood having passed through the absorption paper can effectively be absorbed by the polymer on the water-impermeable outer material side. Combination of the liquid absorption paper and the polymer improves the blood absorption ability.

Figure 9:
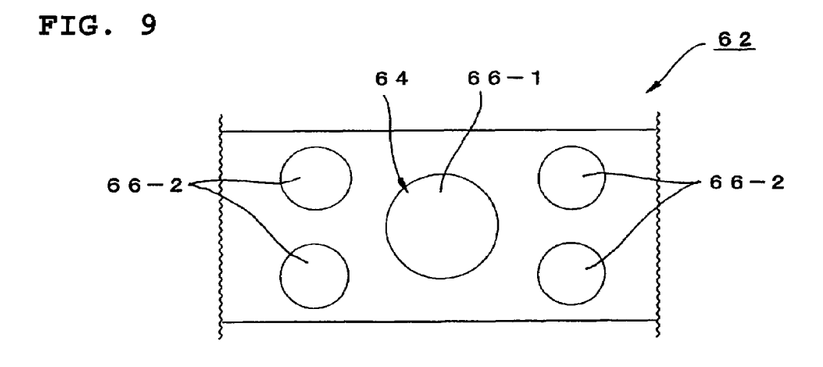
FIG. 9 is a schematic plan view of the polymer formed of the sheet-shaped member according to the seventh embodiment of the present invention.

FIG. 9 illustrates a seventh embodiment of the present invention.

In the previous sixth embodiment, when forming the polymer 52 as the polymeric absorbing material in the sheet shape, the sheet shaped polymer 52 is provided with the penetrating section 54 including a plurality of through-hole sections 56 in the circular shapes having the same diameters. The seventh embodiment is characterized in that, when forming the penetrating section 64 in a sheet-shaped polymer 62 as the polymeric absorbing material, formed are the first and the second through-hole sections 66-1, 66-2 having different diameters.

More particularly, when forming the penetrating section 64 in the polymer 62, as shown in FIG. 9, formed are the first through-hole section 66-1 of a larger diameter and the second through-hole section 66-2 of a smaller diameter.

Accordingly, when the hemostatic tool is applied onto the wound so that the wound is positioned at the center of the water-permeable inner material of the hemostatic tool, the bleeding from the wound passes through the water-permeable inner material and the first pulp-cotton laminated body to the first cortical layer inside of the crust. The blood that has reached the first cortical layer is diffused substantially in a direction orthogonal to the passing direction in the pulp-cotton laminated body, i.e. in the dispersion direction.

The blood diffused by the pulp-cotton laminated body reaches the polymer 62 after passing the second cortical layer, and is absorbed by the polymer 62 that swells and gelates.

At this time, owing to the formation of the first and the second circular through-hole sections 66-1, 66-2 having different diameters in the polymer 62, the first and the second through-hole sections 66-1, 66-2 function as the storage space to store therein the surplus blood, if any, that is not absorbed by the polymer 62, which surplus blood gelates to be in a low viscosity.

Thereby, the first and the second through-hole sections 66-1, 66-2 formed in the polymer 62 function as the expansion swelling space for the polymer 62 absorbing the blood and as the storage space to store the surplus blood gelated with the low viscosity after absorption. Correspondingly to these parts not including the polymer 62, the absorption ability of the polymer 62 is considerably improved as in the sixth embodiment.

Due to formation of the first and the second through-hole sections 66-1, 66-2 in the polymer 62 for improving the blood absorption ability, the blood absorbed by the polymer 62 or the surplus blood stored in the gelate state that has low viscosity does not move out toward the water-permeable inner material on the wound side, i.e. no-counterflowing, in the case where external pressure is applied to the water-impermeable outer material, as in the sixth embodiment. This does not affect the formation of the scab that quickly covers the wound for rapid hemostasis, which is advantageous in practical use.

Further, formation of the first and the second through-hole sections 66-1, 66-2 in the polymer 62 still contributes to improvement of the blood absorption ability, which also contributes to saving the cost of the material corresponding to the through-hole sections, and is advantageous in economical viewpoint.

Still further, by changing the position of the hemostatic tool with respect to the wound in accordance with the forming position of the first and the second through-hole sections 66-1, 66-2 of the polymer 62, the blood absorption ability of the polymer 62, thus the hemostatic tool, can be changed, which can be selectively used based on the state of the wound.

Moreover, instead of the penetrating section including through-hole sections in the polymer, liquid absorption paper with temporary absorption ability can be positioned at a portion of the second cortical layer of the pulp-cotton laminated body on the water-permeable inner material side, and this liquid absorption paper is provided with the penetrating section including the first and the second through-hole sections having the different diameters as a variation of the embodiment.

Accordingly, the liquid absorption paper temporarily absorbs the blood from the water-permeable inner material side and the quick diffusion is achieved utilizing the penetrating section, so that the blood that has passed through the absorption paper can be positively absorbed by the polymer on the water-impermeable outer material side. Combination of the liquid absorption paper and the polymer improves the blood absorption ability. Due to the penetrating section including the first and the second through-hole sections having different diameters, the state of the diffusion can be varied. This contributes to the diffusion ability of the hemostasis tool when changing the position of the hemostatic applied to the wound.

FIGS. 10A–10D illustrate an eighth embodiment of the present invention.

The above sixth and the seventh embodiments are characterized by the penetrating section having the circular through-hole sections formed therein. The eighth embodiment is characterized by a penetrating section 74 having a hole section in an oval or polygonal shape instead of the circle shape in a polymer 72.

Figure 10A:
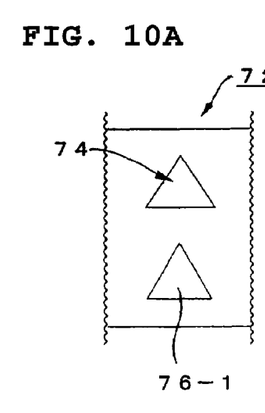
FIG. 10A shows the triangle through-hole section when the through-hole section is formed in the triangle shape.
Figure 10B:
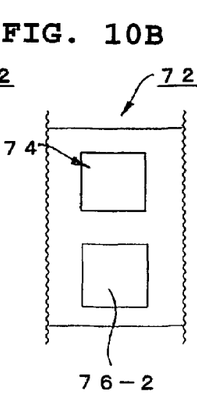
FIG. 10B shows the square through-hole section.
Figure 10C:
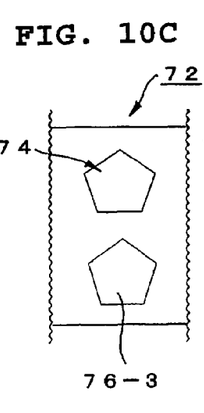
FIG. 10C shows the pentagon through-hole section.
Figure 10D:
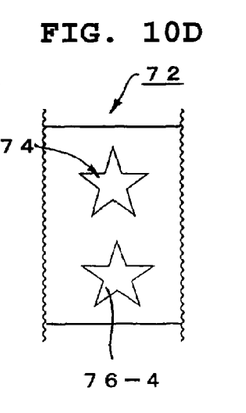
FIG. 10D shows the star-shaped through-hole section 76-4.

More particularly, the penetrating section 74 having the through-hole section in the polygonal shape other than the circle shape includes a triangle through-hole section 76-1 as shown in FIG. 10A, a square through-hole section 76-2 as shown in FIG. 10B, a pentagon through-hole section 76-3 as shown in FIG. 10C, or a star-shaped through-hole section 76-4 as shown in FIG. 10D, which is polygonal or oval shaped hole sections other than the circular shape of the previous embodiment.

Accordingly, when the hemostatic tool is applied onto the wound so that the wound is positioned at the center of the water-permeable inner material of the hemostatic tool, the bleeding from the wound passes through the water-permeable inner material and the first pulp-cotton laminated body to the first cortical layer inside of the crust. The blood that has reached the first cortical layer is diffused substantially in a direction orthogonal to the passing direction in the pulp-cotton laminated body, i.e. in the dispersion direction.

The blood diffused by the pulp-cotton laminated body reaches the polymer 72 after passing the second cortical layer, and is absorbed by the polymer 72 that swells and gelates.

At this time, owing to the formation of the various shaped through-hole sections 76-1 through 76-4 having different diameters in the polymer 72, these various through-hole sections 76-1 through 76-4 function as the storage space to store therein the surplus blood, if any, that is not absorbed by the polymer 72, which surplus blood gelates to be in a low viscosity.

Thereby, the various shaped through-hole sections 76-1 through 76-4 formed in the polymer 72 function as the expansion swelling space for the polymer 72 absorbing the blood and as the storage space to store the surplus blood gelated in the low viscosity after absorption. Correspondingly to these parts not including the polymer 72, the absorption ability of the polymer 72 is considerably improved.

Due to formation of the various shaped through-hole sections 76-1 through 76-4 in the polymer 72 which are provided for improving the blood absorption ability, the blood absorbed by the polymer 72 or the surplus blood that is stored in the gel state having a low viscosity does not move out toward the water-permeable inner material on the wound side, i.e. no-counterflowing, in case external pressure is applied to the water-impermeable outer material, as in the sixth and the seventh embodiments. This does not affect the formation of the scab that quickly covers the wound for rapid hemostasis, which is advantageous in practical use.

Further, formation of the various shaped through-hole sections 76-1 through 76-4 in the polymer 72 still contributes to improvement of the blood absorption ability, which also contributes to saving cost of the material corresponding to these through-hole sections, and is advantageous in an economical viewpoint.

Still further, by changing an appearance of the hemostatic tool for the wound in accordance with the shapes of the various shaped through-hole sections 76-1 through 76-4 of the polymer 72, the blood absorption ability of the polymer 72, and thus the hemostatic tool, can be changed, which can be selectively used based on the state of the wound.

Moreover, instead of the penetrating section including through-hole sections in the polymer, liquid absorption paper with temporary absorption ability can be positioned at a portion of the second cortical layer of the pulp-cotton laminated body on the water-permeable inner material side, and this liquid absorption paper is provided with the polygonal shaped penetrating section 74 as a modification of the embodiment.

Accordingly, the liquid absorption paper temporarily absorbs the blood from the water-permeable inner material side and the quick diffusion is achieved utilizing the penetrating section, so that the blood passed through the absorption paper can be positively absorbed by the polymer on the water-impermeable outer material side. Combination of the liquid absorption paper and the polymer improves the blood absorption ability. Due to the penetrating section 74 in the polygonal shape other than a circle, the state of the diffusion can be varied. This contributes to the diffusion ability of the hemostatic tool when changing the position of the hemostasis applied to the wound.

Figure 11:
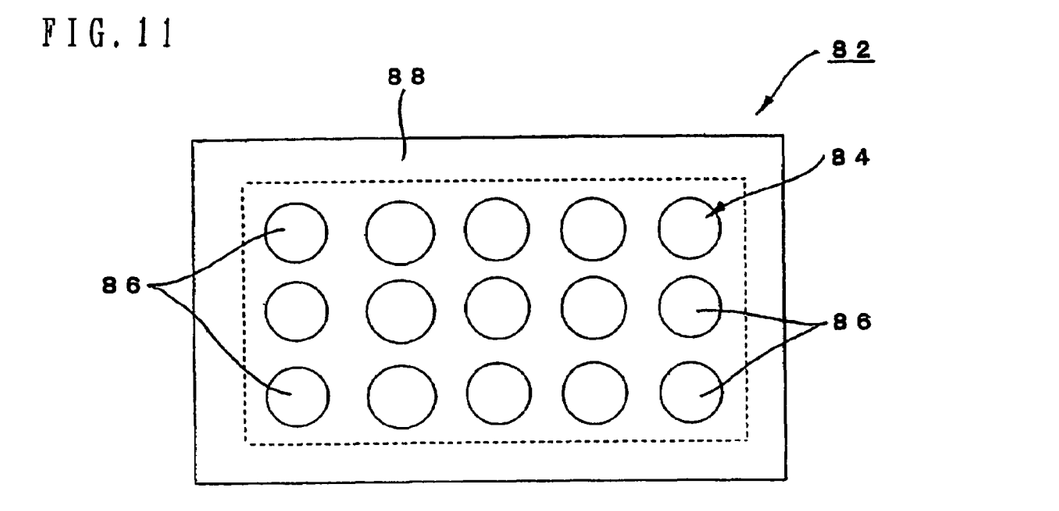
FIG. 11 is a schematic plan view of the polymer formed of the sheet-shaped member according to the ninth embodiment of the present invention.
Figure 12:
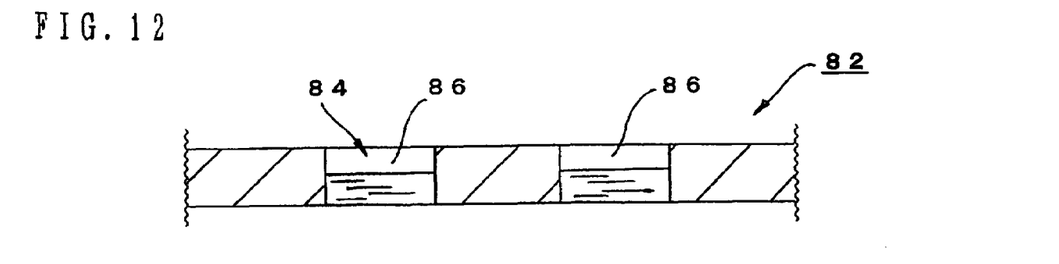
FIG. 12 is a schematic enlarged cross-sectional view of the polymer formed of the sheet-shaped member.

FIGS. 11 and 12 illustrate a ninth embodiment of the present invention.

The ninth embodiment is characterized in that, when forming a penetrating section 84 in a polymer 82, the penetrating sections 84 are gathered in the middle portion spaced apart from the outer rim of the sheet-shaped polymer 82.

More particularly, when forming the penetrating section 84 including a plurality of circular through-hole sections 86 having the same diameters, formed is a region 88 that does not include the penetrating section 84 on the periphery of the polymer 82 as shown in FIG. 11 (see outer portion of dashed-line), and inside of the region 88, the penetrating section 84 or the through-hole sections 86 are gathered.

Accordingly, when the hemostatic tool is applied onto the wound so that the wound is positioned at the center of the water-permeable inner material of the hemostatic tool, the bleeding from the wound passes through the water-permeable inner material and the first pulp-cotton laminated body to the first cortical layer inside of the crust. The blood that has reached the first cortical layer is diffused substantially in a direction orthogonal to the passing direction in the pulp-cotton laminated body, i.e. in the dispersion direction.

The blood diffused by the pulp-cotton laminated body reaches the polymer 82 after passing the second cortical layer, and is absorbed by the polymer 82 that swells and gelates.

At this time, owing to the formation of the penetrating section 86 having the through-hole sections 86 gathered in the middle of the polymer 82, such penetrating section 84 functions as the storage space to store therein the surplus blood, if any, that is not absorbed by the polymer 82, which surplus blood gelates to be in a low viscosity, as shown in FIG. 12.

Thereby, the penetrating section 84 having the through-hole sections 86 gathered in the middle of the polymer 82 functions as the expansion swelling space for the polymer 82 absorbing the blood and as the storage space to store the surplus blood gelated in the low viscosity after absorption. Correspondingly to these parts not including the polymer 82, the absorption ability of the polymer 82 is considerably improved, as in the sixth, seventh, and eighth embodiments.

Due to formation of the penetrating section 84 having the through-hole sections 86 gathered in the middle of the polymer 82 for improving the blood absorption ability, the blood absorbed by the polymer 82 or the surplus blood stored in the gelate state having low viscosity does not move out toward the water-permeable inner material on the wound side, i.e. no-counterflowing, in case external pressure is applied to the water-impermeable outer material, as in the sixth, seventh, and eighth embodiments. This does not affect the formation of the scab that quickly covers the wound for rapid hemostasis, which is advantageous in practical use.

Further, formation of the penetrating section 84 having the through-hole sections 86 gathered in the middle of the polymer 82 still contributes to improvement of the blood absorption ability, which also contributes to saving the cost of the material corresponding to such penetrating section 84, and is advantageous in an economical viewpoint.

Still further, due to the penetrating section 84 having the through-hole sections 86 gathered in the middle of the polymer 82, the polymer 82 has a better blood absorption ability on the periphery portion than in the middle portion. This is comparable to a structure in which only a periphery portion of the polymer 82 is thickened in view of blood absorption ability. Such polymer can withstand for use even if the periphery portion is not adhered. For example, in case a large sized hemostatic tool is formed by connecting a plurality of small sized hemostatic tools, one can use the hemostatic tool by tearing off the parts according to the size of the wound. One can select the hemostatic tool having the proper size according to the state of the wound while maintaining the blood absorption ability of the polymer 62, and thus the hemostatic tool.

Moreover, instead of the penetrating section including the through-hole sections in the polymer, liquid absorption paper with temporary absorption ability can be positioned at a portion of the second cortical layer of the pulp-cotton laminated body on the water-permeable inner material side, and this liquid absorption paper can be provided with the gathered penetrating section in the center portion as a variation of the embodiment.

Accordingly, the liquid absorption paper temporarily absorbs the blood from the water-permeable inner material side and the quick diffusion is achieved utilizing the penetrating section, so that the blood that has passed through the absorption paper can be positively absorbed by the polymer on the water-impermeable outer material side. Combination of the liquid absorption paper and the polymer improves the blood absorption ability. Due to the penetrating section including the through-hole sections gathered in the middle of the liquid paper, the diffusion ability in the middle of the liquid paper can be improved.

FIGS. 13–16 illustrate a tenth embodiment of the present invention.

Figure 13:
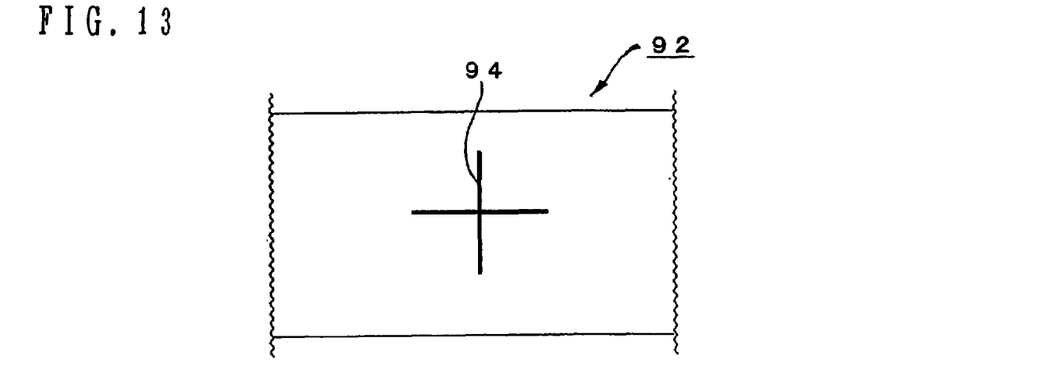
FIG. 13 is a schematic plan view of the polymer formed of the sheet-shaped member before absorption of the blood according to the tenth embodiment of the present invention.
Figure 14:
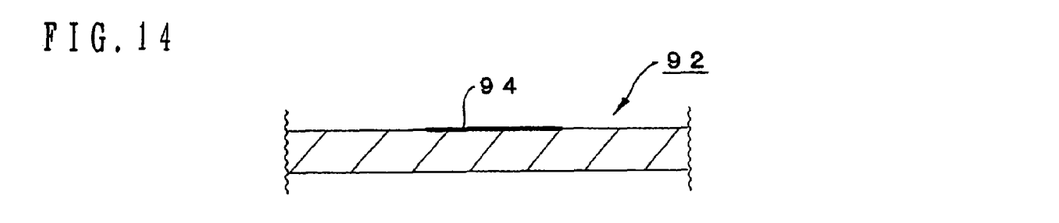
FIG. 14 is a schematic cross-sectional view of the polymer formed of the sheet-shaped member before absorption of the blood.

The tenth embodiment is characterized in that, when forming a polymeric paper 92 that is readily formable into a sheet shape, a penetrating incision 94 which is formed on the surface of the polymeric paper 92, i.e. on the water-permeable inner material side and which is expandable in absorbing the blood.

More particularly, when forming the penetrating incision 94 in the polymeric paper 92, as shown in FIGS. 13 and 14, the penetrating incision 94 is formed in e.g. a cross-shape on the surface of the polymeric paper 92, i.e. on the water-permeable inner material side.

Accordingly, when the hemostatic tool is applied onto the wound so that the wound is positioned at the center of the water-permeable inner material of the hemostatic tool, the bleeding from the wound passes through the water-permeable inner material and the first pulp-cotton laminated body to the first cortical layer inside of the crust. The blood that has reached the first cortical layer is diffused substantially in a direction orthogonal to the passing direction in the pulp-cotton laminated body, i.e. in the dispersion direction.

The blood diffused by the pulp-cotton laminated body reaches the polymeric paper 92 after passing the second cortical layer, and is absorbed by the polymeric paper 92 that swells and gelates.

Figure 15:
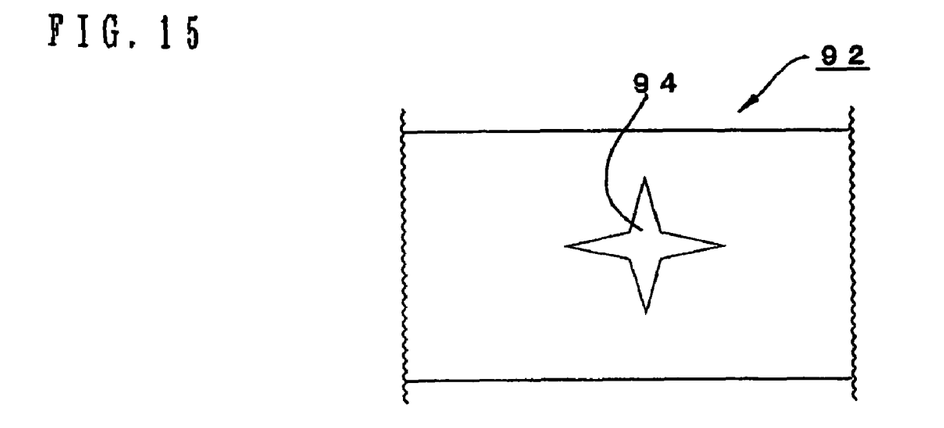
FIG. 15 is a schematic plan view of the polymer formed of the sheet-shaped member after absorption of the blood.
Figure 16:
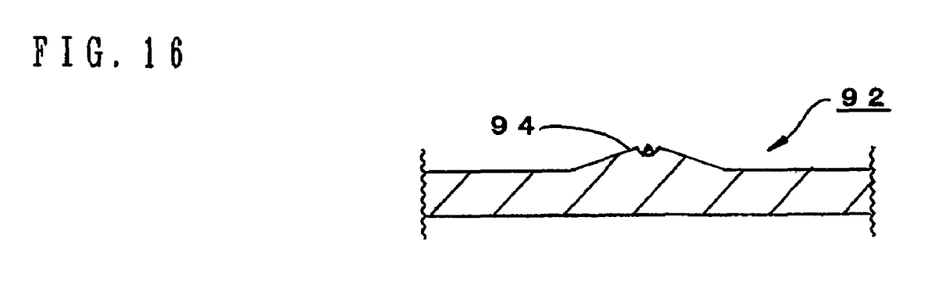
FIG. 16 is a schematic cross-sectional view of the polymer formed of the sheet-shaped member after absorption of the blood.

In case the cross-shaped penetrating incision 94 formed on the surface of the polymeric paper 92, i.e. on the water-permeable inner material side, absorbs the blood to be swollen for gelation, the incision 94 expands so that the polymeric paper 92 absorbs and stores the blood, as shown in FIGS. 15 and 16.

As a result, the cross-shaped penetrating incision 94 formed on the surface of the polymeric paper 92, i.e. on the water-permeable inner material side, expands to contribute to extension of the storage space when the polymeric paper 92 absorbs the blood, which considerably improves the absorption ability of the polymeric paper 92.

Due to formation of the cross-shaped penetrating incision 94 on the surface of the polymeric paper 92, i.e. on the water-permeable inner material side for improvement of the blood absorption ability, the blood absorbed by the polymeric paper 92 does not move out toward the water-permeable inner material on the wound side, i.e. no-counterflowing, in the case where external pressure is applied to the water-impermeable outer material. This does not affect the formation of the scab that quickly covers the wound for rapid hemostasis, which is advantageous in practical use.

Further, formation of the incision 94 e.g. in the cross-shape in the surface of the polymeric paper 92, i.e. on the water-permeable inner material side, permits a simple manufacturing process that saves cost, which is advantageous in an economical viewpoint.

Next, an eleventh embodiment is explained below.

The eleventh embodiment is characterized in that in the hemostatic tool of the lamination construction according to the above-mentioned first embodiment, a synthetic fiber laminated body is employed instead of the pulp-cotton laminated body.

More particularly, in the hemostatic tool for stopping bleeding by absorbing blood from the wound, the lamination comprises the water-permeable inner material on the wound side, the water-impermeable outer material on the side departing from the wound side, the synthetic fiber laminated body between the inner and the outer materials, the crust between the synthetic fiber laminated body and the water-impermeable outer material for diffusing the blood that has passed through the water-permeable inner material and the synthetic fiber laminated body, and the polymer for absorbing the blood diffused by the crust.

Then the synthesis laminated body, by adjusting the net of the synthetic fiber or the size of the mesh, prevents the flow of the clot and erythrocyte in the blood for a quick formation of the scab over the wound, and allows the flow of other components in the blood.

Accordingly, the polymer as a polymeric absorbing material considerably improves the blood absorption ability. The use of the synthetic fiber laminated body applied to the hemostatic tool blocks the flow of the clot and the erythrocyte for rapid covering of the wound by the scab, and allows the flow of the other components such as serum so as to quickly cover the wound by the scab for immediate hemostasis, which is advantageous in practical use.

Further, owing to the smooth surface of the synthetic fiber, the use of the synthetic fiber laminated body, instead of the pulp-cotton lamination, can avoid the serum from staying adjacent the clot. In case the external pressure is applied to the hemostatic tool when the serum stays adjacent the clot, the staying serum can be flown from the expanded synthetic fiber laminated body to the polymer side, which avoids undesirable counterflowing of the staying serum to the clot side. This is due to the fact that the synethetic fiber lamination has higher elasticity than the pulp-cotton lamination and permits flexible expansion and contraction of the mesh size of the synthetic fiber laminated body.

The present invention is not limited to above-mentioned first through eleventh embodiments, but is adaptable for various applications and variations or modifications.

For example, a hemostatic agent can be applied onto the crust on the wound side when the hemostatic tool is laminated with the water-permeable inner material, the first pulp-cotton laminated body, the crust, the polymer, the second pulp-cotton laminated body, and the water-impermeable outer material in turn from the wound side, and when adhering the periphery of the water-permeable inner material and the water-impermeable outer material, in order to adhere with the adherence method such as the sheet-heel method.

That is, the effect of the hemostatic agent is added to the hemostatic tool for treating the wound.

The hemostatic tool and the agent permit rapid formation of the scab to achieve quicker hemostasis.

Although the first through fifth embodiments are explained as a single set of crust, more than one set of crust can be employed as a special configuration.

That is, two or more crusts are laminated to form the hemostatic tool.

Due to the two or more crusts disposed in the intermediate layer of the hemostatic tool, the passing blood is more effectively diffused, taking advantage of the wide area of the hemostatic tool to effect the full absorption ability.

Accordingly, the charcoals in at least the part of the laminated body of the two or more crusts achieve deodorization and antibacterial effect, and a negative air ions effect can be expected, which is easy on the human body.

Further when forming the hemostatic tool, an alternative member, instead of the first pulp-cotton laminated body, can be employed which contributes to formation of the scab as a special configuration.

For the formation of the scab, it is required that the blood is separated into the blood coagulating components and uncoagulating blood components; the clot is left over the wound; and the serum (liquid that does not coagulate) is quickly sent toward the crust side that absorbs and diffuses, so that the wound is provided with the clot as soon as possible. By using the synthetic fiber or other materials, the alternative member is formed in a tight net or in a small mesh.

Thereby, the alternative member in the small mesh allows exclusive pass of the serum and blocks the clot, so that the clot is placed on the wound side for rapid formation of the scab to achieve quicker hemostasis.

Further, when forming the hemostatic tool, an alternative liquid absorbing material including a paper member, cloth member, or synthetic fabric member having liquid absorption ability can be utilized instead of the crust.

That is, instead of the crust, the alternative liquid absorbing materials of various materials are used to utilize the liquid absorption ability.

Due to the liquid absorption ability of the alternative liquid absorption material, the serum in the blood is quickly absorbed to contribute to cover the wound. Absorption of the liquid helps the diffusion of the alternative liquid absorption material, which considerably improves the blood absorption ability.

Also if the hemostatic tool has the structure having the pulp-cotton laminated body on the water-impermeable outer material side of the polymer, formation of the penetrating section in the pulp-cotton laminated body permits this section to function as an expansion space for the polymer that absorbed the blood and swelled and gelated, which considerably improves the blood absorption ability of the polymer. The blood absorbed by the polymer does not move out toward the water-permeable inner material on the wound side, i.e. no-counterflowing, in the case where external pressure is applied to the water-impermeable outer material. This does not affect the formation of the scab that quickly covers the wound for rapid hemostasis, which is advantageous in practical use.

What is claimed is:

1. A hemostatic tool for stopping bleeding by absorbing blood from a wound and having blood diffusion and absorption abilities, which includes lamination comprising
   a water-permeable inner material on a wound side,
   a water-impermeable outer material on an outer side departing from the wound side,
   a pulp-cotton laminated body between the inner and outer materials,
   a crust between the pulp-cotton laminated body and the water-impermeable outer material for diffusing the blood having passed through the water-permeable inner material and the pulp-cotton laminated body, and
   a polymer for absorbing the blood diffused by the crust.

2. The hemostatic tool according to claim 1, wherein the water-permeable inner material includes a water-permeable film, artificial skin, or suture material.

3. The hemostatic tool according to claim 1, wherein the crust includes the pulp-cotton laminated body interposed between two paper-made cortical layers.

4. The hemostatic tool according to claim 1, wherein the hemostatic tool includes a tear-off line that can be torn off in a certain shape when lamination from the water-permeable inner material to the water-impermeable outer material is formed.

5. The hemostatic tool according to claim 1, wherein the crust includes a powder charcoal dispersed in at least a part of the pulp-cotton laminated body interposed between the two paper-made cortical layers.

6. The hemostatic tool according to claim 1, wherein if the water-permeable inner material is formed with the water-permeable film, the water-permeable film includes a semi-permeable membrane structure which allows passing of the blood from the side on the wound and blocks passing of liquid from the other side.

7. The hemostatic tool according to claim 1, wherein the polymer is formed of a sheet-shaped member in which a penetrating section is defined.

8. The hemostatic tool according to claim 7, wherein the penetrating section includes a plurality of through-hole sections penetrating the polymer.

9. The hemostatic tool according to claim 8, wherein the through-hole section include a circular hole section having the same diameters.

10. The hemostatic tool according to claim 8, wherein the through-hole section include a circular hole sections having different diameters.

11. The hemostatic tool according to claim 8, wherein the through-hole sections include hole sections in polygonal shape other than the circular shape.

12. The hemostatic tool according to claim 7, wherein the penetrating section is gathered toward a center portion spaced apart from the periphery of the polymer.

13. The hemostatic tool according to claim 7, wherein the penetrating section is formed in the polymer on the water-permeable inner material side, and the penetrating section includes a penetrating incision that is expandable when absorbing the blood.

14. A hemostatic tool for stopping bleeding by absorbing blood from the wound, which includes lamination comprising a water-permeable inner material on a wound side, a water-impermeable outer material on an outer side departing from the wound side, a synthetic fiber laminated body between the inner and outer materials, a crust between the synthetic fiber laminated body and the water-impermeable outer material for diffusing the blood having passed through the water-permeable inner material and the synthetic fiber laminated body, and a polymer for absorbing the blood diffused by the crust.

* * * * *